(12) United States Patent
Wei et al.

(10) Patent No.: US 12,079,930 B2
(45) Date of Patent: Sep. 3, 2024

(54) METHOD AND SYSTEM FOR DRAWING BRAIN FUNCTIONAL ATLAS

(71) Applicant: Beijing Galaxy Circumference Technologies Co., Ltd, Beijing (CN)

(72) Inventors: Coach Kecheng Wei, Beijing (CN); Haiyang Li, Beijing (CN); Qingyu Hu, Beijing (CN)

(73) Assignee: BEIJING GALAXY CIRCUMFERENCE TECHNOLOGIES CO., LTD, Beijing (CN)

( * ) Notice: Subject to any disclaimer, the term of this patent is extended or adjusted under 35 U.S.C. 154(b) by 155 days.

(21) Appl. No.: 17/781,595

(22) PCT Filed: Oct. 19, 2020

(86) PCT No.: PCT/CN2020/121817
§ 371 (c)(1),
(2) Date: Jun. 1, 2022

(87) PCT Pub. No.: WO2021/109727
PCT Pub. Date: Jun. 10, 2021

(65) Prior Publication Data
US 2022/0414979 A1     Dec. 29, 2022

(30) Foreign Application Priority Data
Dec. 2, 2019 (CN) .......................... 201911214999.9

(51) Int. Cl.
*G01V 3/00* (2006.01)
*G01R 33/48* (2006.01)
(Continued)

(52) U.S. Cl.
CPC .......... *G06T 17/00* (2013.01); *G01R 33/4806* (2013.01); *G06T 11/20* (2013.01); *G16H 30/40* (2018.01); *G06T 2210/41* (2013.01)

(58) Field of Classification Search
CPC .............. G01R 33/543; G01R 33/5659; G01R 33/3415; G01R 33/36; A61B 5/055
(Continued)

(56) References Cited

U.S. PATENT DOCUMENTS 9,662,039 B2    5/2017    Liu et al.
2009/0279762 A1*   11/2009   Tsukimoto ....... G01R 33/56341
                                                    382/131
(Continued)

FOREIGN PATENT DOCUMENTS

CN         105117731 A     12/2015
CN         106055881 A   * 10/2016
(Continued)

OTHER PUBLICATIONS

Development of a fast method for calculating self volume of brain areas using multi Atlas method and large site segmentation, Progress in Medicine, vol. 39, No. 8, pp. 833-840, ISSN: 0287-3648 (Aug. 2019).

*Primary Examiner* — Walter L Lindsay, Jr.
*Assistant Examiner* — Frederick Wenderoth
(74) *Attorney, Agent, or Firm* — Meunier Carlin & Curfman LLC

(57) ABSTRACT

A method and system for drawing a brain functional atlas. The method includes: initializing a brain functional atlas of an individual by using a brain functional atlas template to obtain an initial individualized brain functional atlas; dividing the initial individualized brain functional atlas into a plurality of large areas, each large area including a plurality of functional areas; entering iteration, each iteration process
(Continued)

including calculating the connection degree between each voxel in each large area and each functional area in the large area in sequence, and adjusting each voxel to the functional area having the highest connection degree with the voxel until all voxels are adjusted; and when an ending condition is satisfied, ending the iteration to obtain a final individualized brain functional atlas.

16 Claims, 10 Drawing Sheets

(51) Int. Cl.
*G06T 11/20* (2006.01)
*G06T 17/00* (2006.01)
*G16H 30/40* (2018.01)

(58) Field of Classification Search
USPC .......................................................... 324/309
See application file for complete search history.

(56) References Cited

U.S. PATENT DOCUMENTS

2013/0279772 A1* 10/2013 Stedele ................. A61B 34/10
 382/128
2015/0272468 A1* 10/2015 Liu ...................... A61B 5/0042
 600/410

FOREIGN PATENT DOCUMENTS

| CN | 107330948 A | 11/2017 |
| CN | 111081351 A | 4/2020 |
| JP | 2015054218 A | 3/2015 |

* cited by examiner

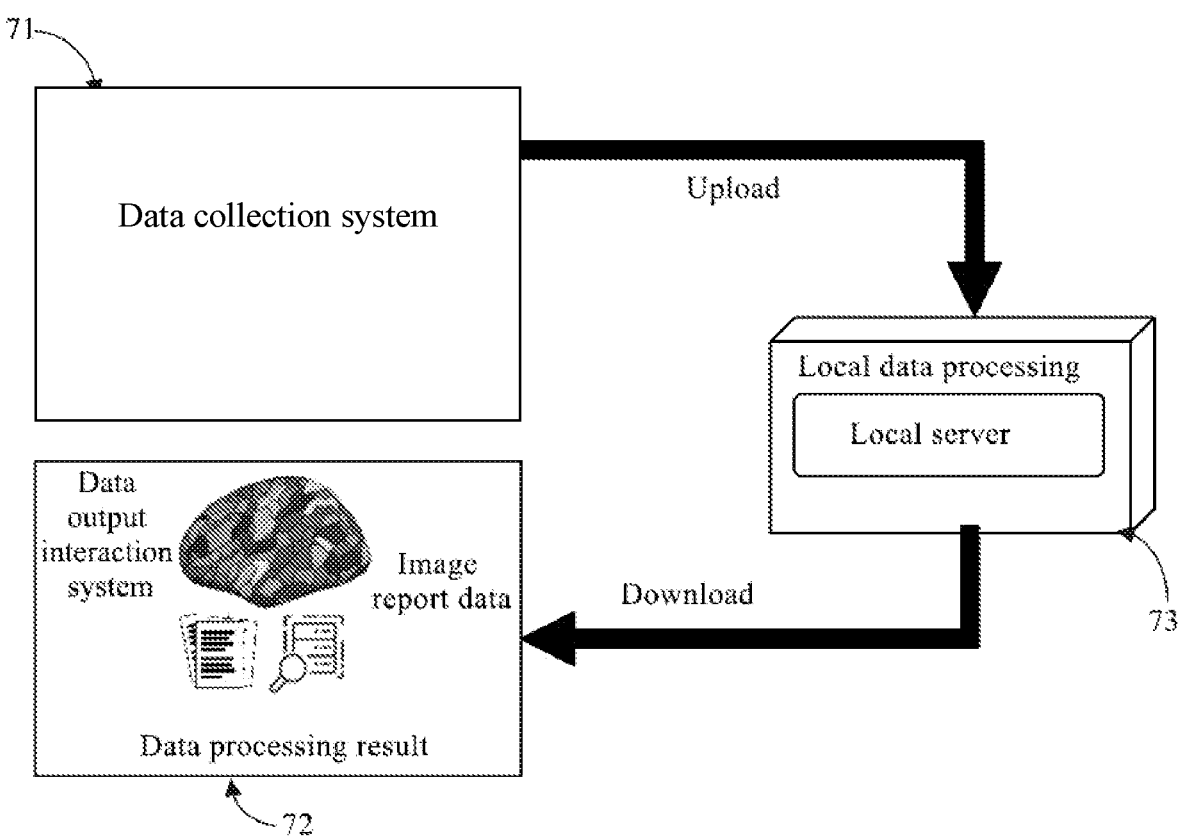
Fig. 7-A

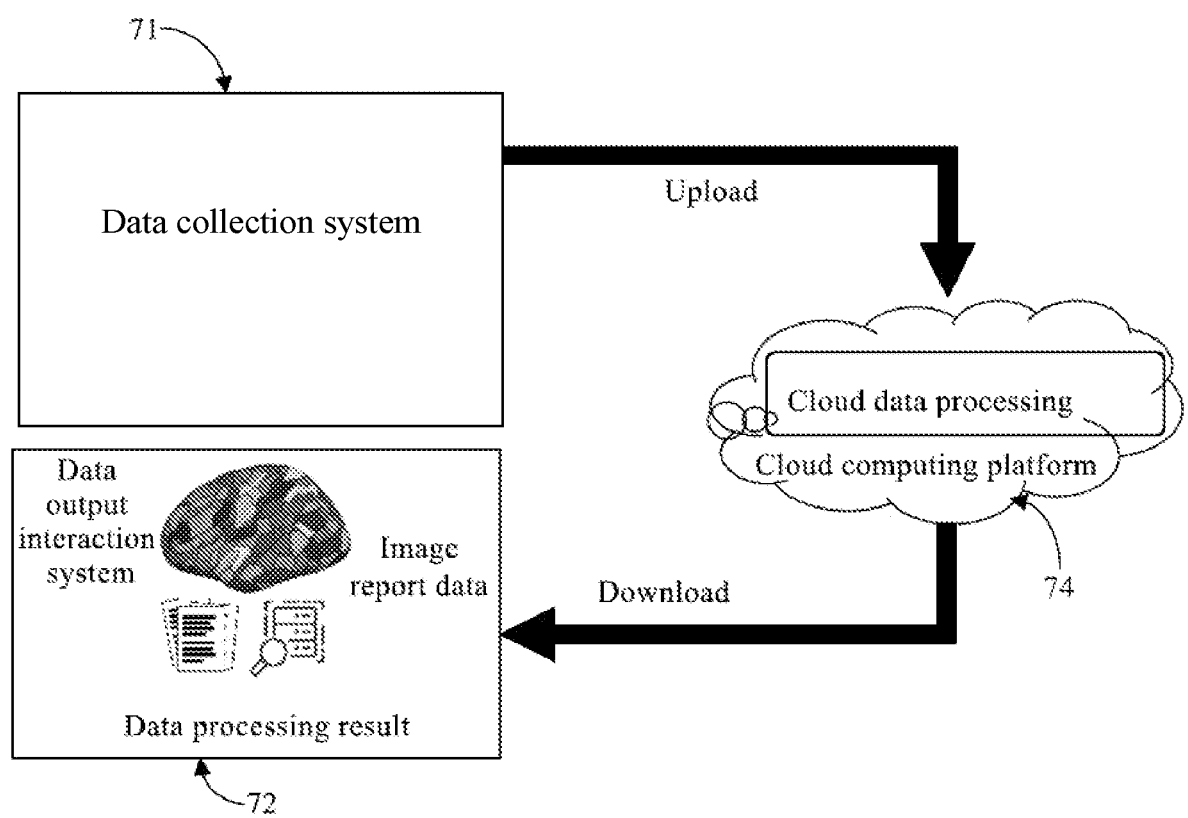
Fig. 7-B

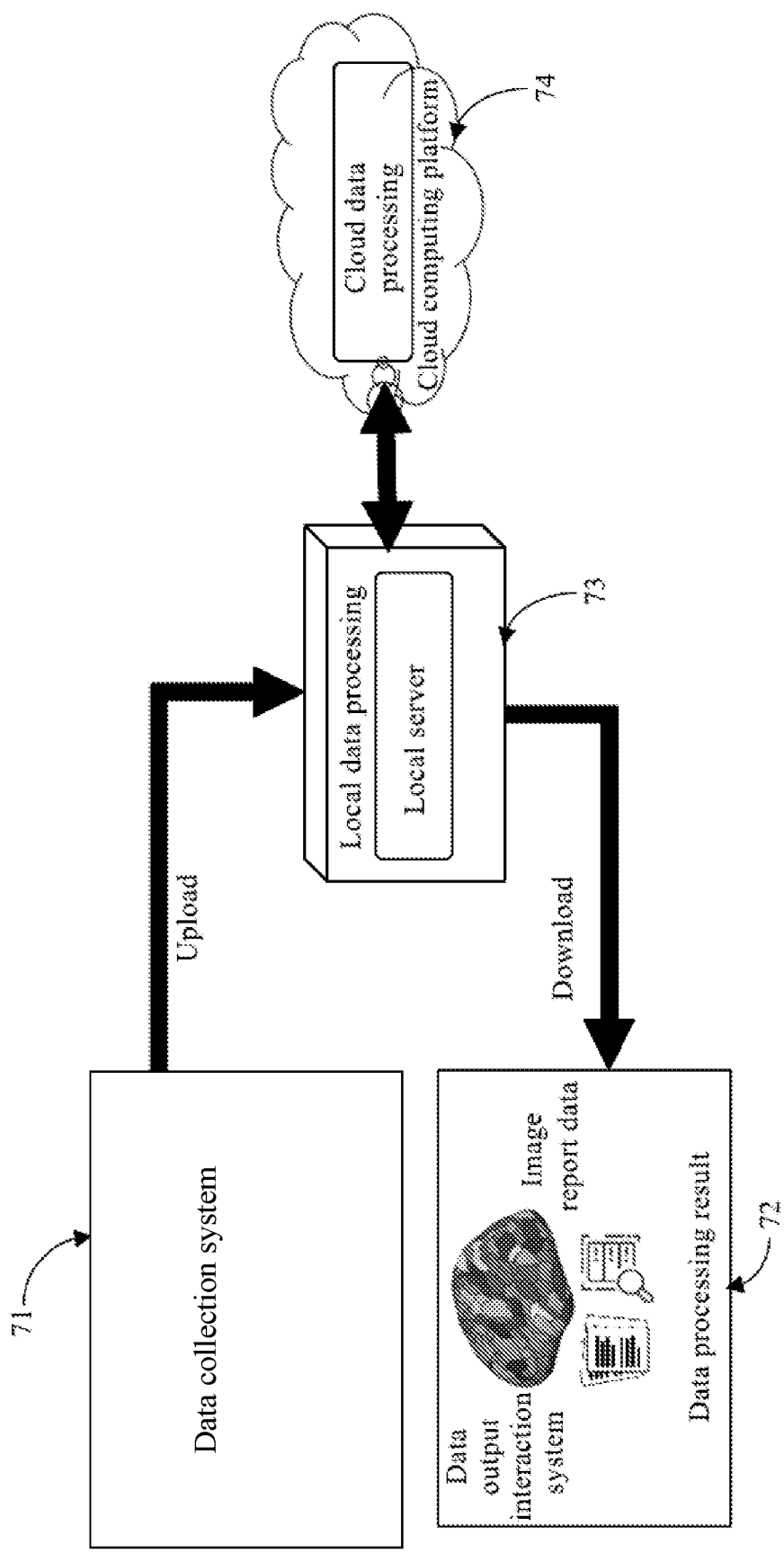
Fig. 7-C (a) A brain functional atlas drawn by a method of the present disclosure
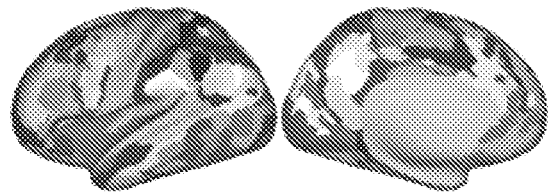
(b) A brain functional atlas drawn by a method in the prior art
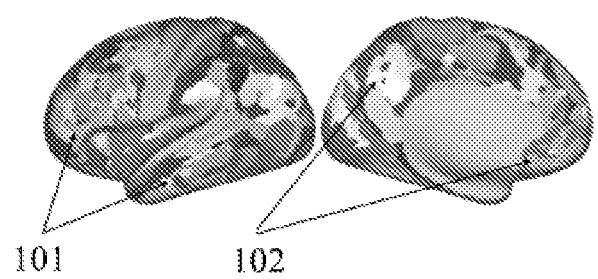
101    102
Fig. 11

METHOD AND SYSTEM FOR DRAWING BRAIN FUNCTIONAL ATLAS

CROSS-REFERENCE TO RELATED APPLICATIONS

This application is a National Stage of International Application No. PCT/CN2020/121817, filed Oct. 19, 2020, which claims priority to Chinese Patent Application No. 201911214999.9, filed Dec. 2, 2019, both of which are hereby incorporated by reference in their entireties.

FIELD

The present disclosure relates to the technical field of medical image processing, in particular to a method and system for drawing a brain functional atlas.

BACKGROUND

In the 19th century, Korbinian Brodmann, a German neuroanatomist, first drawn the human brain atlas (Brodmann Brain Atlas), pointing out that different areas of the brain are responsible for different functions, Since then, brain atlases have been an important direction for brain science research. Flow the human brain is partitioned, the boundaries of the areas and the connections between these areas have important implications for basic brain science and clinical research.

For a long time, because of the lack of understanding of the human brain and technical limitations, brain atlases can only be drawn in a "group level" approach, i.e., studying the brains of a group of people and conducting statistical analysis to draw an "average" atlas. A "group level" brain atlas can reveal many human commonalities and patterns, which is very meaningful in scientific research. The "group level" brain atlas, which currently represents the US brain atlas, was published in Nature by Glasser et al. in 2016 (Glasser et al, Nature, A multi-modal parceilation of human cerebral cortex, 2016).

SUMMARY

A first aspect of the present disclosure provides a method for drawing a brain functional atlas. The method includes: initializing a brain functional atlas of an individual by using a brain functional atlas template to obtain an initial individualized brain functional atlas, the initial individualized brain functional atlas dividing the brain of the individual into a plurality of functional areas; dividing the initial individualized brain functional atlas into a plurality of large areas, each of the large areas comprising a plurality of functional areas; entering an iteration, the iteration comprising: calculating a connection degree between each voxel in each of the large areas and each of the functional areas in the each of the large areas in sequence, and adjusting each voxel to a functional area having the highest connection degree with the each voxel until all voxels are adjusted; and ending the iteration to obtain a final individualized brain functional atlas in response to an ending condition being satisfied.

In a first possible implementation, the iteration includes: calculating a reference time series signal of each of the functional areas based on time series signals of all voxels in the each of the functional areas; determining an unadjusted voxel as a current voxel; calculating a correlation value between a time series signal of the current voxel and a reference time series signal of each of the functional areas in a current large area, the correlation value serving as a connection degree between the current voxel and each of the functional areas in the current large area, and the current large area being a large area to which the current voxel belongs; adjusting the current voxel to a functional area having the highest connection degree with the current voxel; judging whether all voxels have been adjusted once, and returning to the determining an unadjusted voxel as a current voxel in response to all voxels not being adjusted once; ending the iteration in response to all voxels being adjusted once.

In combination with the first possible implementation, in a second possible implementation, before the entering the iteration, the method further includes: initializing credibility of each of the voxels; after the adjusting the current voxel to the functional area having the highest connection degree with the current voxel, the method further includes: updating a credibility of the current voxel; and the calculating a reference time series signal of each of the functional areas comprises: calculating an average value of time series signals of all voxels with a credibility not lower than a preset threshold in each of the functional areas as the reference time series signal of the functional area, or calculating a median of time series signals of all voxels with a credibility not lower than a preset threshold in each functional area as the reference time series signal of the functional area.

In combination with the second possible implementation, in a third possible implementation, the updating the credibility of the current voxel includes: selecting a largest correlation value and a second largest correlation value from calculated correlation values of the time series signal of the current voxel and the reference time series signal of each of the functional areas in the current large area; and calculating and updating the credibility of the current voxel, the credibility of the current voxel being equal to a ratio of the largest correlation value to the second largest correlation value.

In combination with the first aspect or any of the first to third possible implementations of the first aspect, in a fourth possible implementation, the ending the iteration includes: ending the iteration in response to a preset iteration frequency or convergence criterion being reached.

In combination with the first aspect or any one of the first to fourth possible implementations of the first aspect, in a fifth possible implementation, a group level brain functional atlas is preselected or generated as the brain functional atlas template.

In combination with the first aspect or any one of the first to fifth possible implementations of the first aspect, in a sixth possible implementation, the step of preselecting or generating the group level brain functional atlas as the brain functional atlas template includes: dividing the brain into a plurality of large areas; calculating a group level functional connectivity profile in each of the large areas, the functional connectivity profile being a functional connectivity matrix of voxels in the each of the large areas and N interest regions in the each of the large area, and N being a natural number; dividing each of the large areas into a plurality of fine-grained functional partitions via a clustering algorithm based on the functional connectivity profile as a feature; comprehensively evaluating an index of the clustering algorithm and an index of maximization functional homogeneity to determine a quantity of local optimal partitions; and merging the fine-grained functional partitions in each of the large areas via a merging algorithm to create the group level brain functional atlas of the whole brain as the required brain functional atlas template.

In combination the first aspect or any of the first to fifth possible implementations of the first aspect, in a seventh possible implementation, the dividing the initial individualized brain functional atlas into the plurality of large areas includes: dividing the initial individualized brain functional atlas into ten large areas by dividing each of the left cortex and right cortex of the brain into five areas: frontal lobe, parietal lobe, occipital lobe, temporal lobe and pan-central sulcus.

A second aspect of the present disclosure providers method for drawing a group level brain functional atlas. The method includes:
  obtaining brain magnetic resonance scanning data of a group of people;
  dividing a brain into a plurality of large areas;
  calculating a group level functional connectivity profile in each of the large areas, the group level functional connectivity profile being a functional connectivity matrix of all voxels in each of the large areas and N interest regions in each of the large areas, and N being a natural number;
  dividing each of the large areas into a plurality of fine-grained functional partitions via a clustering algorithm based on the group level functional connectivity profile as a feature;
  comprehensively evaluating an index of the clustering algorithm and an index of maximization functional homogeneity to determine a quantity of local optimal partitions; and
  merging the fine-grained functional partitions in each of the large areas via a merging algorithm to create the group level brain functional atlas of the whole brain.

In a possible implementation of the second aspect, the calculating the group level functional connectivity profile includes:
  calculating individualized functional connectivity profiles in each of the large areas, the group level functional connectivity profile being the functional connectivity matrix of the voxels in the each of the large areas and the N interest regions in the each of the large areas, and N being a natural number; and
  calculating an average value of all individualized functional connectivity profiles in each of the large areas to obtain the group level functional connectivity profile.

A third aspect of the present disclosure provides a system for drawing a brain functional atlas. The system includes: an initialization module, configured to initialize a brain functional atlas of an individual by using a brain functional atlas template to obtain an initial individualized brain functional atlas, the initial individualized brain functional atlas dividing a brain into a plurality of functional areas; a preprocessing module, configured to divide the initial individualized brain functional atlas into a plurality of large areas, each of the large areas comprising a plurality of functional areas; and an iteration processing module, configured to enter iteration, the iteration comprising: calculating a connection degree between each voxel in each of the large areas and each of the functional areas in the each of the large areas in sequence, and adjusting each voxel to a functional area having the highest connection degree with the each voxel until all voxels are adjusted; and end the iteration in response to an ending condition being satisfied to obtain a final individualized brain functional atlas.

A fourth aspect of the present disclosure provides a data processing system. The data processing system includes a processor and a memory. The memory is configured to store computer-executable instructions, and when the data processing system is running, the processor executes the computer-executable instructions stored in the memory to enable the data processing system to implement the method for drawing the brain functional atlas according to the first aspect or any one of possible implementations of the first aspect.

A fifth aspect of the present disclosure provides a medical image processing system. The medical image processing system includes: a data collection system, a data output interaction system, and the data processing system according to the third aspect, where
  the data collection system is configured to collect magnetic resonance scanning data of an individual, and upload the collected data to the data processing system;
  the data processing system is configured to implement any method for drawing the brain functional atlas according to the first aspect to obtain a final individualized brain functional atlas, and generate a corresponding report and/or image based on the final individualized brain functional atlas;
  the data output interaction system is configured to obtain the report and/or image from the data processing system, and display the report and/or image; and
  the data processing system includes a local server and/or a cloud computing platform, and in response to the data processing system includes both the local server and the cloud computing platform, the local server and the cloud computing platform jointly implement the method for drawing the brain functional atlas according to the first aspect or any one of possible implementations of the first aspect based on load balancing strategies and/or shared strategies.

A sixth aspect of the present disclosure provides a computer-readable storage medium storing one or more programs. The one or more programs include computer-executable instructions that, when executed by a data processing system including a processor, enable the data processing system to implement the method for drawing the brain functional atlas according to the first aspect or any one of possible implementations of the first aspect.

BRIEF DESCRIPTION OF THE DRAWINGS

In order to illustrate the technical solutions of the embodiments of the present disclosure more clearly, the accompanying drawings that are used in the description of the embodiments will be briefly introduced below.

FIG. 7-A is a network architecture diagram of a medical image processing system including a local server according to an embodiment of the present disclosure.

FIG. 7-B is a network architecture diagram of a medical image processing system including a cloud computing platform according to an embodiment of the present disclosure.

FIG. 7-C is a network architecture diagram of a medical image processing system including the local server and the cloud computing platform according to an embodiment of the present disclosure.

FIG. 11 is a brain functional atlas drawn by an embodiment of the present disclosure and a brain functional atlas drawn by U.S. Pat. No. 9,662,039 B2.

DETAILED DESCRIPTION OF THE EMBODIMENTS

Figure 1:
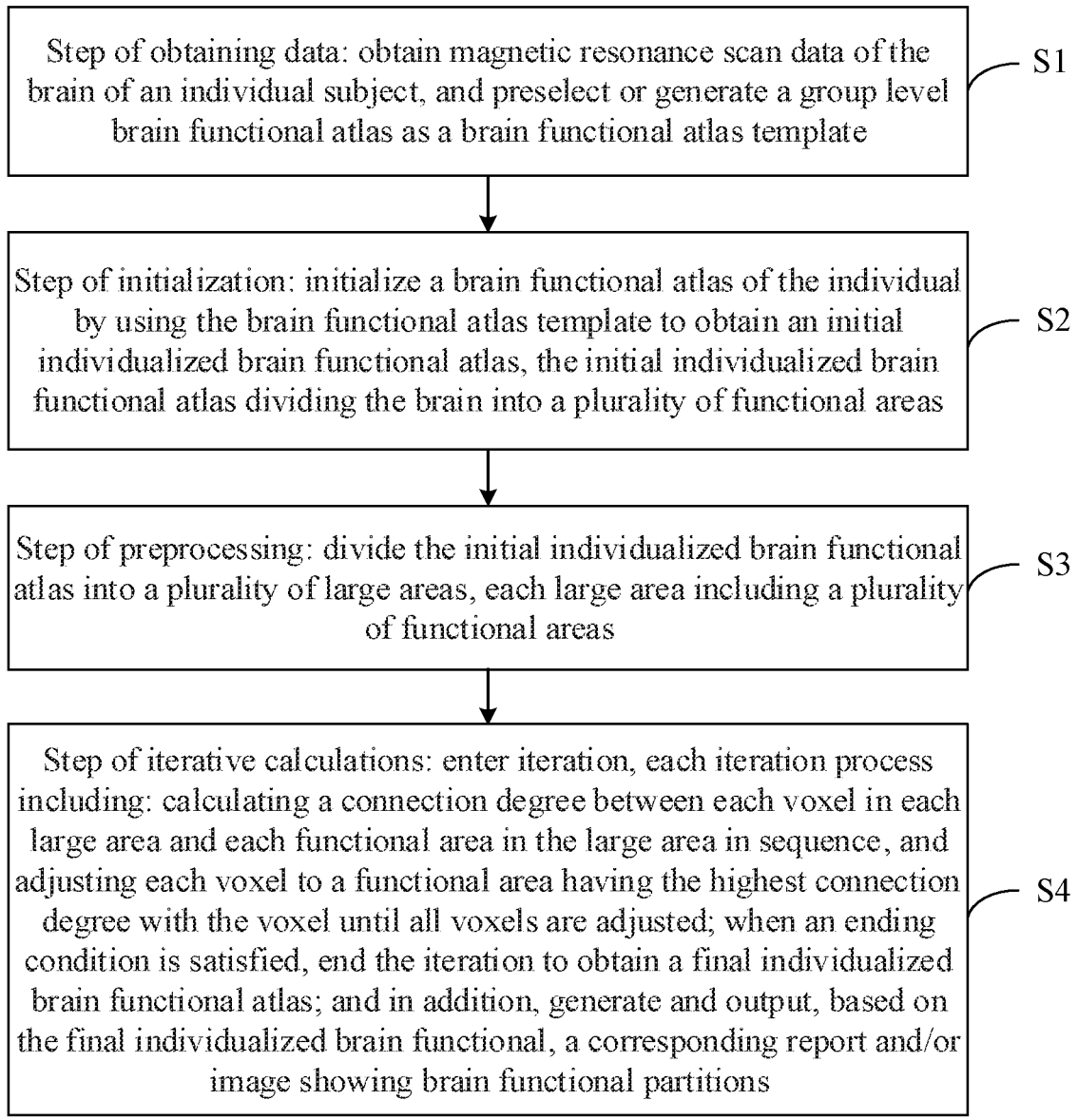
FIG. 1 is a schematic flow diagram of a method for drawing a brain functional atlas according to an embodiment of the present disclosure.

In order to make those skilled in the art better understand the solutions of the present disclosure, the technical solutions in the embodiments of the present disclosure will be clearly and completely described below with reference to the accompanying drawings in the embodiments of the present disclosure. It is apparent that the described embodiments are only a part of embodiments of the present disclosure, but not all embodiments. Based on the embodiments of the present disclosure, all other embodiments obtained by those of ordinary skill in the art without any creative work shall fall within the protection scope of the present disclosure.

The terms "comprise" and "have" and any variations thereof in the description and claims of the present disclosure and the above accompanying drawings are intended to cover non-exclusive inclusions. For example, a process, method, system, product or device comprising a series of steps or units is not limited to the listed steps or units, but optionally also includes unlisted steps or units, or optionally also includes other steps or units inherent to the process, method, product or device.

For ease of understanding, some terms involved in the present disclosure are introduced first.

A brain functional atlas, referred to as a "brain atlas" or "brain map" or "functional atlas" or "brain functional network atlas", refers to an atlas in which the cerebral cortex is functionally partitioned and different areas of the brain responsible for different functions are marked. The areas marked are also referred to as "functional areas" or "functional networks".

An individualized brain functional atlas, referred to as an individualized brain atlas for short, is a representation of a brain functional atlas of an individual.

A group level brain functional atlas, referred to as a group level brain atlas for short, is a representation of a statistical brain functional atlas of a group of people.

A brain functional network is a representation of brain functional connectivity.

Functional magnetic resonance imaging (fMIR), referred to as functional magnetic resonance or magnetic resonance for short, shows areas of the brain that are activated in response to external stimuli.

Task functional magnetic resonance imaging (task fMRI) involves asking subjects to perform a given task (for example, moving their tongue) during a magnetic resonance imaging scan in the hope that the brain areas or networks responsible for that task may be located via magnetic resonance.

A voxel is short for a volume pixel. Conceptually similar to the smallest unit of two-dimensional space, a pixel, used in image data of a two-dimensional computer image, the voxel is the smallest unit of digital data in 3d space segmentation, and is used in 3d imaging, scientific data and medical imaging.

A Blood Oxygen Level Dependency (BOLD) signal is a blood oxygen level signal collected by functional magnetic resonance imaging.

Time series signal of a voxel: during functional magnetic resonance imaging, BOLD signals are typically collected for each voxel for a period of time (for example, two minutes), and the BOLD signals in this time period are time series signals of the voxel.

A region of interest (ROI) is a region to be processed in machine vision and image processing, which is outlined from a processed image in the form of boxes, circles, ellipses, irregular polygons, etc.

A Pearson's correlation coefficient is used to measure whether two data sets are on the same line, that is, to measure the linear relationship between distance variables. A calculation formula is as follows:

$$\rho_{X,Y} = \frac{\operatorname{cov}(X, Y)}{\sigma_X \sigma_Y} = \frac{E((X - \mu_X)(Y - \mu_Y))}{\sigma_X \sigma_Y} = \frac{E(XY) - E(X)E(Y)}{\sqrt{E(X^2) - E^2(X)} \sqrt{E(Y^2) - E^2(Y)}}.$$

The formula is defined as: a Pearson correlation coefficient ($\rho_{x,y}$) of two continuous variables (X, Y) is equal to the covariance cov(X,Y) divided by the product of their standard deviations ($\sigma_x$, $\sigma_y$). Coefficients are always between −1.0 and 1.0. Variables close to 0 are regarded to be uncorrelated, and variables close to 1 or −1 are regarded to be strongly correlated.

The present disclosure will be described in detail below through specific embodiments.

Referring to FIG. 1, an embodiment of the present disclosure provides a method for drawing a brain functional atlas. The method may include the following steps.

S1, the step of obtaining data: magnetic resonance scan data, for example, functional magnetic resonance scan data, such as a BOLD signal, which correlates with a functional area of the brain, or structural magnetic resonance scan data, such as a magnetic resonance T1 signal, which correlates with the brain structure, of the brain of an individual subject are obtained, and a group level brain functional atlas is preselected or generated as a brain functional atlas template.

Functional magnetic resonance imaging is an emerging neuroimaging method. Its principle is to use magnetic resonance imaging to measure changes in blood oxygen level caused by neuronal activity and collect BOLD signals. At present, functional magnetic resonance imaging is mainly used to study functional activities of human and animal brain or other nervous systems. Resting state functional magnetic resonance imaging refers to the individual subject lying in a magnetic resonance scanner in a resting state, the whole body relaxed, without doing any task or systematic thinking for scanning. In particular, the present disclosure may use resting state functional magnetic resonance scan data as original data to draw a brain functional atlas. The functional magnetic resonance scan data are based on fourdimensional imaging data of voxels, including time series signals (BOLD signals) of all voxels.

It is necessary to obtain the group level brain functional atlas in advance. The group level brain functional atlas is used as the brain functional atlas template to initialize a brain functional atlas of an individual. The brain functional atlas template divides a brain into a plurality of functional areas. For example, the quantity is 56, 112, etc. Optionally, the brain functional atlas template may divide the brain into a plurality of large areas according to structural information. Preferably, the brain is divided into two large areas: a left cortex and a right cortex. Preferably, the brain is divided into two large areas: a senior cortex and an inferior cortex. More preferably, the brain is divided into four large areas: the left cortex, the right cortex, the senior cortex, and the inferior cortex. More preferably, the left cortex and the right cortex of the brain are each divided into five large areas according to structural information: frontal lobe, parietal lobe, occipital lobe, temporal lobe, and pan-central sulcus, in this way, the brain is divided into ten large areas. All functional areas belong to these large areas, and each large area includes a plurality of functional areas.

S2, the step of initialization: the brain functional atlas of the individual is initialized by using the brain functional atlas template to obtain an initial individualized brain functional atlas, the initial individualized brain functional atlas dividing the brain into a plurality of functional areas.

In the step of initialization, the initial individualized brain functional atlas may be obtained by projecting functional partitions of the brain functional atlas template to the reconstructed cerebral cortex of the individual for each large area of the brain structure. The "projection" is to complete one-to-many, many-to-many, and many-to-one registration by means of interpolation and other mathematical methods through the point-level mapping relationship between different images of the same individual. Different registration methods (rigid, radial, nonlinear, etc.) use different formulas and constraints. For example, the BBR algorithm provided by Douglas Greve et al, is a commonly used "projection" method (Douglas Greve and Bruce Fishl, Accurate and robust brain image alignment using boundary based registration, NeuroImage 2009).

Due to individual differences, the initial individualized brain functional atlas does not reflect real brain functional partitions of the individual, and subsequent iterative calculations are required to improve the precision and individual precision.

S3, the step of preprocessing: the initial individualized brain functional atlas is divided into a plurality of large areas, each large area including a plurality of functional areas. "A plurality of" means at least two.

For example, the initial individualized brain functional atlas may be divided into ten large areas by dividing each of the left cortex and the right cortex of the brain into five large areas: the frontal lobe, parietal lobe, occipital lobe, temporal lobe and pan-central sulcus. For another example, the brain may be divided into four areas: the senior cortex, the inferior cortex, the left cortex, and the right cortex.

In the step of preprocessing, the credibility of each voxel may also be initialized, the credibility representing the degree of credibility of a voxel functionally belonging to a current functional area. Optionally, an initial value of the credibility of each voxel may be set to 1 via initialization. In subsequent iterative calculations, the credibility may be continuously updated.

S4, the step of iterative calculations: iteration is entered. Each iteration process includes: a connection degree between each voxel in each large area and each functional area in the large area is calculated in sequence, and each voxel is adjusted to a functional area having the highest connection degree with the voxel until all voxels are adjusted; and the iteration is ended when an ending condition is satisfied to obtain a final individualized brain functional atlas. In addition, a corresponding report and/or image showing functional partitions of the brain may be generated and output based on the final individualized brain functional atlas.

The step of iterative calculations is a process of repeated iterative calculations. All voxels are adjusted in each iteration. After an iterative process is ended, whether an ending condition is satisfied is judged. If not, an output result of the previous iterative process is used as input to enter the next iteration, and all voxels are adjusted again. The final individualized brain functional atlas is output until the ending condition is satisfied.

In the final individualized brain functional atlas, each voxel has been adjusted many times and is adjusted to the most possible functional area, so high precision is achieved. By setting an appropriate iteration ending condition, a better balance between precision and calculation time may be achieved, and an extremely high-precision final individualized brain functional atlas may be obtained.

Optionally, whether a convergence criterion is satisfied or whether a preset iteration frequency is reached may be used as the iteration ending condition. The iteration is ended when the preset iteration frequency or the convergence criterion is reached.

Optionally, one convergence criterion is: the change between two iterations is very small, for example, the change between two iterations is less than 1%, preferably less than 0.1% or 0.5%, etc. Optionally, another convergence criterion is: all reliability reaches a certain threshold. According to experience, the threshold may be, for example, 2 to 10, preferably 3, 4 or 5. Optionally, the preset frequency may be, for example, 5 to 1000, preferably 100, 150, or 200.

Optionally, the connection degree between each voxel in each large area and each functional area in the large area may be calculated by using a correlation value of a time series signal of the voxel and a reference time series signal of the functional area. The correlation value represents the correlation, correlation coefficient, or degree of similarity between the time series signal of the voxel and the reference time series signal of the functional area. The more similar the two (time series signal of the voxel and a reference time series signal of the functional area) are, the higher the correlation value is, indicating that the closer the two are, the higher (or larger or stronger) connection degree the two have.

Further, the correlation value may be calculated by adopting a variety of correlation calculation methods, which are not limited herein. For example, a Pearson correlation value of the time series signal of the voxel and the reference time series signal of the functional area may be calculated to represent the connection degree between the voxel and the functional area.

Figure 2:
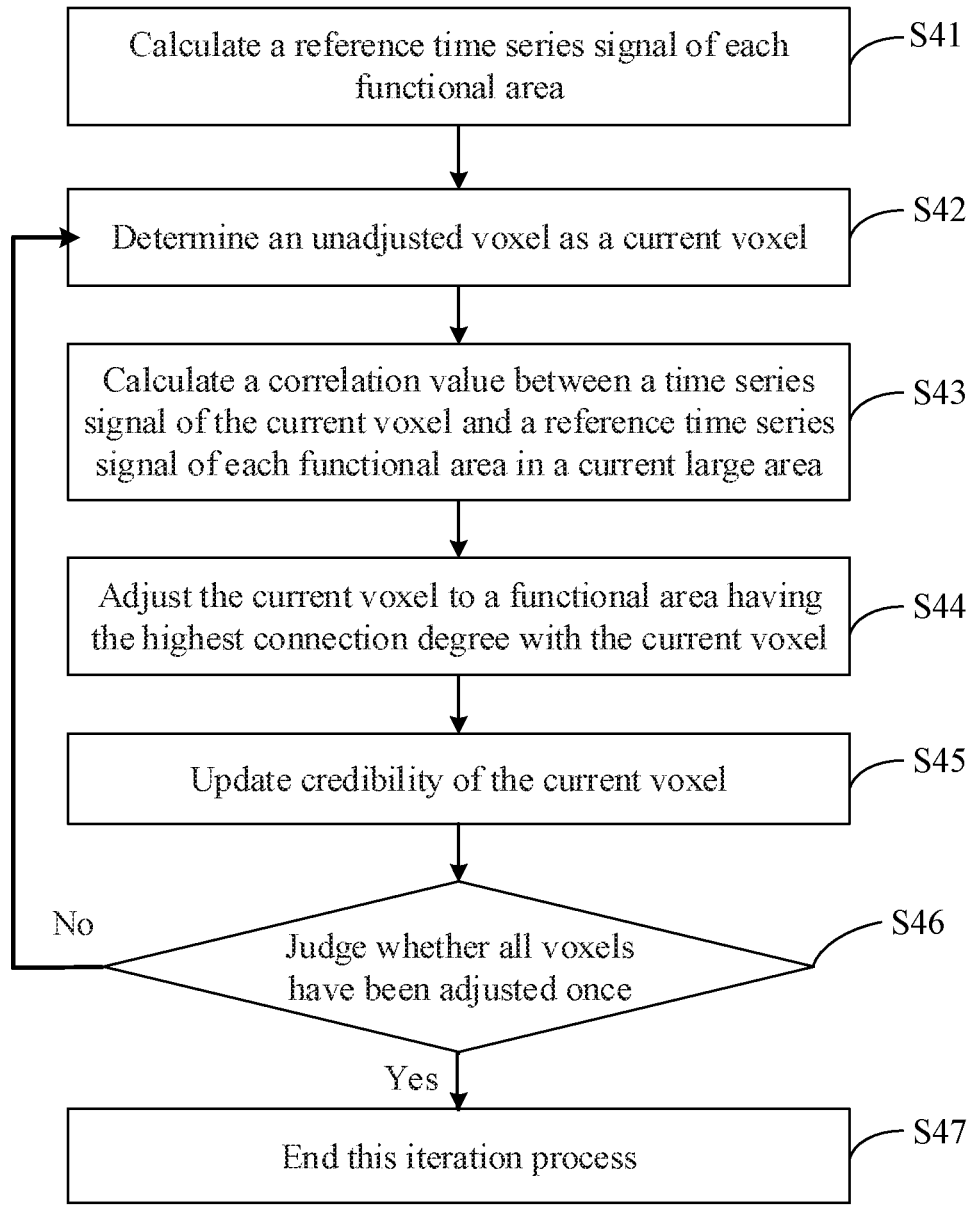
FIG. 2 is a schematic flow diagram of each iteration process according to an embodiment of the present disclosure.

Referring to FIG. 2, in some implementations, each iteration process may include followings.

S41, a reference time series signal of each functional area is calculated based on time series signals of all voxels in the functional area. For example, an average value or median of time series signals of all voxels with credibility not less than a preset threshold in each functional area may be calculated as the reference time series signal of the functional area. Optionally, after a first iteration, the average value or median of the time series signals of all voxels in each functional area may be calculated as the reference time series signal of the functional area.

S42, an unadjusted voxel is determined as a current voxel.

S43, a correlation value between a time series signal of the current voxel and a reference time series signal of each functional area in a current large area is calculated. The correlation value is used as a connection degree between the current voxel and each functional area in the current large area. The current large area is a large area to which the current voxel belongs.

S44, the current voxel is adjusted to a functional area having the highest connection degree with the current voxel.

By adjusting the voxel to the functional area having the highest connection degree (namely, the maximum correlation value) with the voxel, the precision of division of the functional areas is improved, and the individualized brain functional atlas is updated. Optionally, if there are a plurality of equal maximum correlation values, the current voxel may be adjusted or reallocated to any one of the functional areas with the maximum correlation value.

S45, the credibility of the current voxel is updated.

Optionally, the largest correlation value and the second largest correlation value may be selected from the obtained correlation values of the time series signal of the current voxel and the reference time series signal of each functional area in the current large area; and the credibility of the current voxel is calculated and updated, where the credibility of the current voxel is made to be equal to a ratio of the largest correlation value to the second largest correlation value.

S46, whether all the voxels have been adjusted once is judged. If no, S42 is performed, the next voxel is selected, and S43 and S44 above continue to be performed. If yes, S47 is performed.

S47, if all voxels have been adjusted once, the iteration process is ended.

The end of each iteration process indicates that the individualized brain functional atlas has been adjusted and updated once. Then, if the iteration ending condition has not been satisfied, the next iteration process is started based on an updated individualized brain functional atlas obtained in this iteration process.

Figure 3:
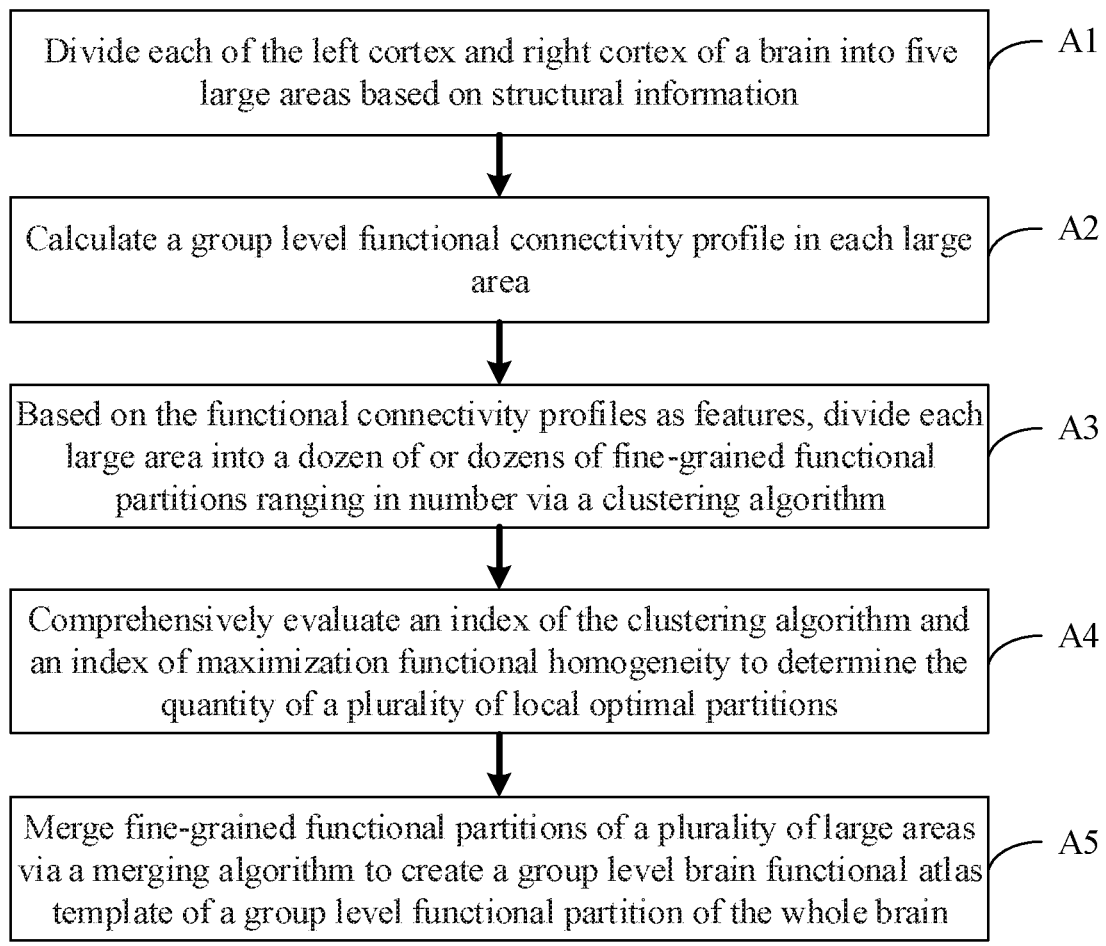
FIG. 3 is a schematic flow diagram of generating a group level brain functional atlas template according to an embodiment of the present disclosure.

Referring to FIG. 3, in some embodiments, after collecting functional magnetic resonance scan data of a group, a group level brain functional atlas may be generated as a brain functional atlas template by the following method. The method includes the following steps.

A1, the brain is divided into a plurality of large areas according to structural information. Optionally, the brain may be divided into the ten large areas by dividing each of the left cortex and the right cortex of the brain into five large areas: the frontal lobe, parietal lobe, occipital lobe, temporal lobe and pan-central sulcus.

A2, a group level functional connectivity profile, namely a functional connectivity matrix of voxels in an area and a plurality of regions of interest (ROI) in the large area, is calculated in each large area. The operation may be performed by the following steps.

① For a voxel in each large area of each individual, a functional connectivity degree of the voxel to each ROI in the large area is calculated to obtain a multi-dimensional vector, such as a 1000-dimensional vector, or a 4098-dimensional vector. Optionally, the ROI may be obtained by uniform sampling.

② The average of a plurality of vectors of each voxel in each large area of all individuals in the group is calculated to obtain a group level functional connectivity vector of each voxel, and the functional connectivity vectors of all voxels form a matrix to obtain a group level functional connectivity profile (or group level functional connectivity matrix).

A3. Based on the functional connectivity profiles as features, each voxel in each large area is classified via a clustering algorithm, and finally each large area is divided into a dozen to dozens of "classes" (fine-grained functional partitions) ranging in number. The clustering algorithm includes but is not limited to K-means and related algorithms, a spectral clustering algorithm, and a Gaussian Mixed Model.

A4, an index of the clustering algorithm and an index of maximization functional homogeneity are comprehensively evaluated to determine the quantity of a plurality of local optimal partitions. For example, the index of the clustering algorithms is that based on the "distance" in a 1000-dimensional space between voxels, voxels that are close to the "distance" are divided into the same fine-grained functional partition, thereby achieving "local optimal".

A5, fine-grained functional partitions of a plurality of large areas are merged via a merging algorithm to create a template of a group level functional partition of the whole brain. The merging algorithm includes but is not limited to direct splicing merging, and edge trimming and edge voxel reallocation are performed after splicing. The obtained group level brain functional atlas template may have different resolutions, ranging from dozens of functional areas to hundreds of functional areas.

It can be understood that the above solution of the embodiment of the present disclosure may be implemented in a local or cloud data processing system such as a local server and a cloud computing platform.

In order to facilitate better understanding of the technical solution provided by the embodiments of the present disclosure, the following description is made by taking an implementation in a specific scenario as an example.

Figure 4:
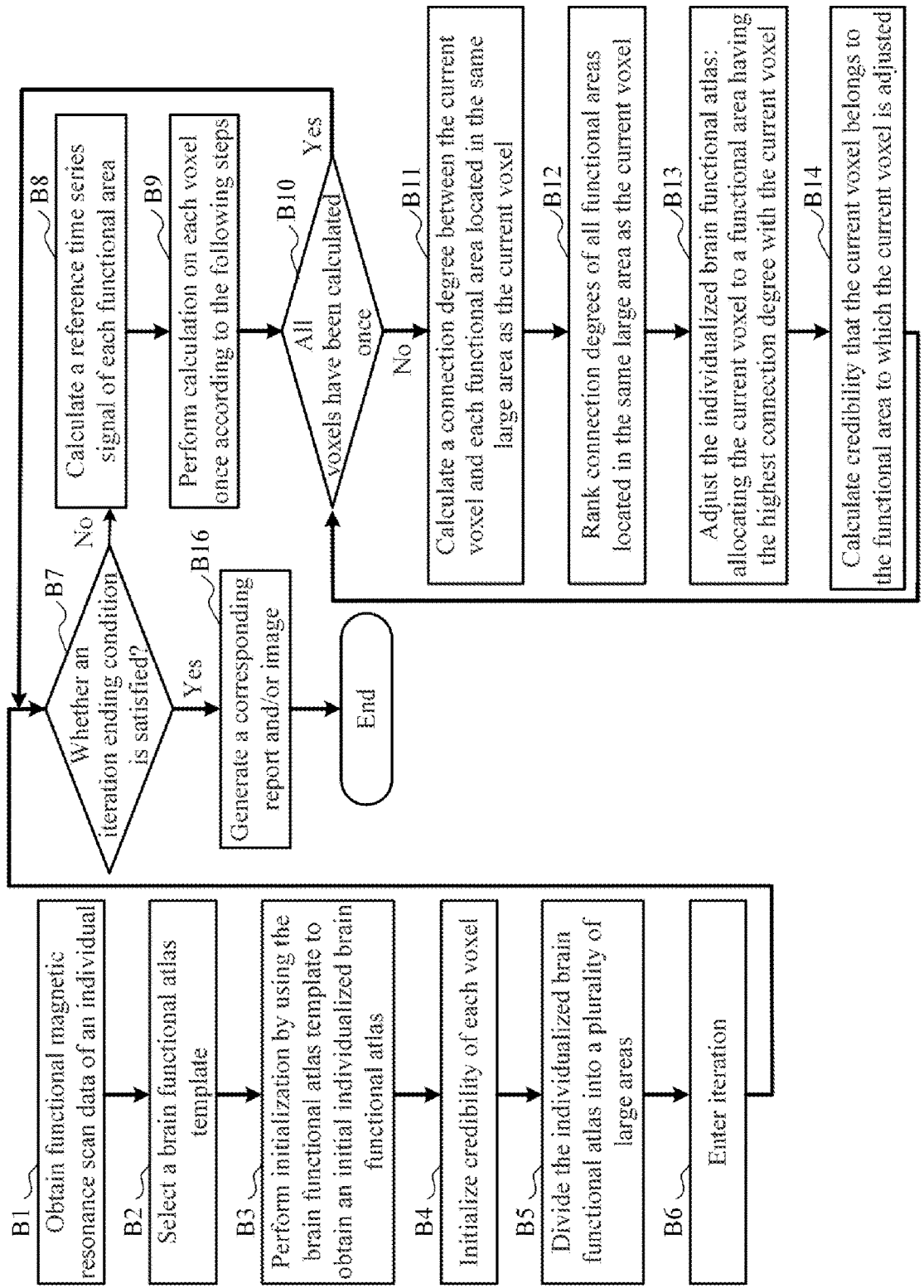
FIG. 4 is a schematic flow diagram of an embodiment of a specific application scenario of the present disclosure.

FIG. 4 is a flow diagram of a method for drawing a brain functional atlas in an embodiment of a specific application scenario. The method includes the following steps.

B1, functional magnetic resonance scan data of an individual are obtained, including time series signals of all voxels.

B2, a brain functional atlas template is selected.

B3, a brain functional atlas of the individual is initialized by using the brain functional atlas template to obtain an initial individualized brain functional atlas.

B4, the credibility of each voxel is initialized into the maximum credibility, namely 1.

B5, the individualized brain functional atlas is divided into a plurality of local areas, namely a plurality of large areas, each large area including a plurality of functional areas.

B6, iteration is entered.

B7, whether an iteration ending condition is satisfied is judged, if not, step B8 is executed, and if yes, step B16 is executed.

B8, reference signals (short for reference time series signals) of all functional areas are calculated: for each functional area, voxels with credibility not lower than a certain threshold are selected to calculate a reference time series signal of the functional area.

B9, calculation is performed on each voxel once according to the following steps in sequence.

B10, whether all the voxels have been calculated once is judged, if yes, step B7 is executed again, and if not, the next voxel that has not been calculated or adjusted is determined as a current voxel, and step B11 is executed.

B11, the connection degree between the current voxel and each functional area located in the same large area as the current voxel is calculated.

B12, connection degrees of all functional areas located in the same large area as the current voxel are ranked.

B13, the individualized brain functional atlas is adjusted: the current voxel is allocated to the functional area having the strongest connection degree with the current voxel.

B14, the credibility that the current voxel belongs to the functional area to which the current voxel is adjusted is calculated.

B15 step B10 is executed again.

B16, if the iteration ending condition is satisfied, the iteration is ended, and a corresponding report and/or image is generated.

Therefore, in some feasible implementations of the present disclosure, the method for drawing the brain functional atlas is provided. According to the method, by performing iterative calculations on the initial individualized brain functional atlas, and continuously adjusting a functional area to which each voxel belongs via the iterative process, a high-precision individualized brain functional atlas can be drawn finally, and high stability, high reliability, and low noise can be achieved under different precisions or resolutions.

It should be noted that according to the present disclosure, division of large areas is performed first, and then voxels are adjusted or reallocated in each large area by taking the large area as a unit. Compared with the manner of individuation of the whole brain that directly allocates voxels in the whole brain, the manner of individuation of large areas has the advantages that on the one hand, the general rules of neuroscience such as "voxels in the same fine-grained functional partition should belong to the same large area" are naturally introduced as additional information of partitions for voxel adjustment in each large area, which effectively improves the anti-noise and anti-interference capacity; and on the one hand, because the voxel adjustment is performed in each large area which is such a small range, the processing precision and calculation speed can be improved effectively.

In the practice of the present disclosure, the whole brain may be divided into 56 functional areas, 112 functional areas, 213 functional areas and other different precisions, and results are stable and reliable, and have been successfully clinically verified.

Figure 8:
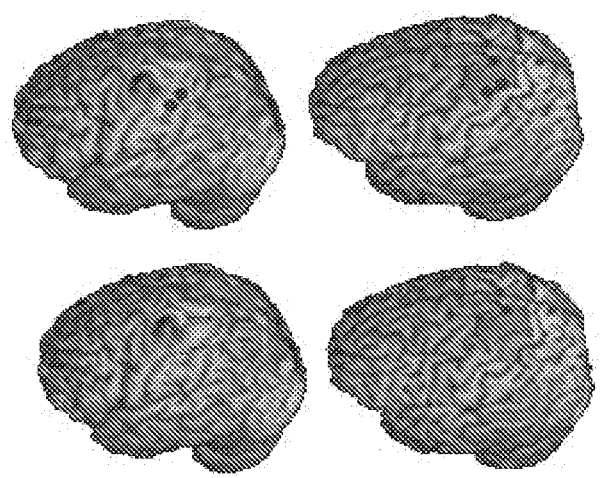
FIG. 8 is a clinical verification result of a brain functional area drawn by the present disclosure and a brain functional area measured by ECS.

Verification method 1: referring to FIG. 8, the left column in FIG. 8 is the cerebral cortex of one person, and the right column is the cerebral cortex of another person. The first line is to position a functional area by using an intraoperative electrical cortical stimulation (ECS) technology (namely a clinical method commonly used to locate a functional area). The second line is to position a functional area by using the method of the present disclosure. It can be seen that the position of the functional area located by the method of the present disclosure is consistent with the position of the functional area located by the ECS technology, which verifies accurate positioning of the present disclosure.

Figure 9:
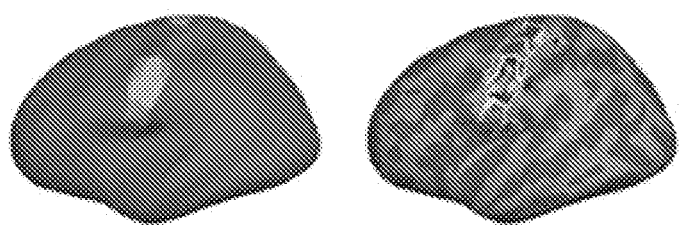
FIG. 9 is a clinical verification result of a brain functional area drawn by the present disclosure and a brain functional area measured by long-time sampling of task nuclear magnetism.

Verification method 2: referring to FIG. 9, a motion network is verified. Different colored parts are part of the motion network. For example, one part controls the movement of the hands, and another part controls the movement of the body (the face, head, tongue).

In FIG. 9, the right column is a motion network diagram sampled by a large number of experiments using a traditional method (task functional nuclear magnetic). A specific positioning method is to let healthy people perform tasks under a functional nuclear magnetic scan, such as moving their tongue or pinching fingers during the scan. Brain functional areas associated with the movements are positioned after 1.5 hours of exercise and 10 consecutive days of scans. Due to the large quantity of experimental samples, the method may accurately find a corresponding functional area.

In FIG. 9, the left column is the method of the present disclosure. It can be seen that a positioning area on the left is basically the same as a positioning area on the right, and the yellow boundary in the figure on the right is a result of comparison between the present disclosure and the figure on the right, showing that movement functional networks obtained by the two methods have a quite high contact ratio. In addition, the present disclosure does not require any task, and the sampling time is short (20 minutes is enough on a 3T magnetic resonance machine), which has obvious advantages over task functional nuclear magnetism. Confirmation of individualized brain functional areas within a short period is more conducive to clinical applications.

Figure 10:
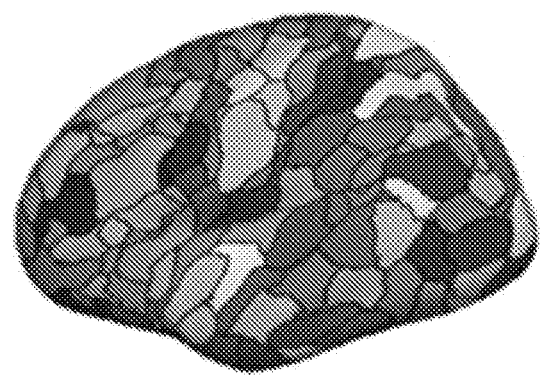
FIG. 10 is a brain functional atlas drawn by an embodiment of the present disclosure.

FIG. 10 is a brain functional atlas obtained by using a specific drawing method of the present disclosure. The drawing steps are as follows: structural and resting state functional magnetic resonance scans were performed on a young normal subject, and signal preprocessing is performed. A group level brain atlas template of 213 functional areas was selected for initialization, that is, group level partitions were projected onto the individual cerebral cortex via nonlinear registration. The individual cerebral cortex is divided into five areas on the left and right according to the structure: frontal lobe, parietal lobe, occipital lobe, temporal lobe and pan-central sulcus, and then individualized calculation iterations are performed on each large area on the individual cerebral cortex. Taking 17 functional partitions of the left frontal lobe as an example: at a first iteration of individuation, time series signals of all voxels in each functional partition were initialized and averaged to obtain an average signal as a reference signal of the partition, and there are 17 reference signals in total. Then Pearson coefficients of the time series signals of each voxel in the left frontal lobe and the 17 reference signals were calculated as correlation values, and the 17 correlation values were ranked in a descending order. The voxel is reallocated to a functional partition having the highest correlation value and the credibility is calculated. The credibility is the ratio of the largest correlation value to the second largest correlation value, and the value range of the credibility is [1, +∞). It is set as high credibility to allocate the voxel to the functional area when the credibility is ≥3. For example, a correlation value between a 110th voxel and a partition 10 is 0.78, the maximum correlation value, and a correlation value between the 110th voxel and a partition 8 is 0.18, the second largest correlation value, so the credibility is 0.78/0.18=4.3, which means a great confidence in allocating the voxel to the partition 10. For another example, a functional connectivity degree between a 125th voxel and the partition 8 is 0.35, the strongest functional connectivity degree, and a functional connectivity degree between the 125th voxel and a partition 4 is 0.29, the second strongest functional connectivity degree, so the credibility is 0.35/0.29=1.2, which means a lack confidence in allocating the voxel to the partition 8. The above operations are repeated for all voxels to complete the first individualized update. Starting from a second iteration, 17 reference signals are recalculated each time. The reference signal at this time is obtained by averaging time series signals of voxels with credibility greater than 3 in each partition. If there is no voxel with credibility greater than 3 in the partition, voxels with the top 5% highest credibility in the partition are selected instead. Each voxel in the large area is reallocated to a partition according to correlation values with the reference signals, and subjected to credibility estimation. After all voxels in the large area are updated, the next iteration is entered, and iteration is ended until the similarity of individualized partition results of two iterations reaches 99% or above, or after 110 iterations are completed. Finally, after all the large areas are individualized, the 10 large areas are merged via a direct merging method. Till then, the calculation of individualized functional partitions is completed, and the individualized brain functional atlas with the 213 functional areas is obtained. A boundary line is added to the boundary of each functional area of the individualized brain functional atlas to more clearly distinguish each functional area.

FIG. 11 is an effect comparison diagram of a brain functional atlas drawn by adopting the method of the present disclosure and a brain functional atlas drawn by the related art.

As shown in (a) on the left in FIG. 11, functional areas are drawn by using the method of the present disclosure, and the brain is divided into the functional areas in a manner of individuation of large areas. As shown in (b) on the right side of FIG. 11, functional areas are drawn by using the technical solution of U.S. Pat. No. 9,662,039B2, and the brain is divided into the functional areas in a manner of simultaneous individuation of the whole brain.

As shown in the diagram, there is a lot of obvious noise in (b) on the right, as shown by 101 and 102 in the figure. Noise is a small area in the figure that violates neuroscience principles. Neuroscience principles include: at the same resolution, there should generally be no other functional areas within a functional area of the nervous system. If green appears in a red area, it indicates that there is a problem with a processing result. The boundary of each functional area generally has a certain degree of smoothness. If the boundary is jagged, or there are a plurality of discontinuous areas in a functional area, it is usually caused by the noise interference in a processing method.

In order to better implement the above solution in the embodiments of the present disclosure, related apparatuses for implementing the above solution are also provided below.

Figure 5:
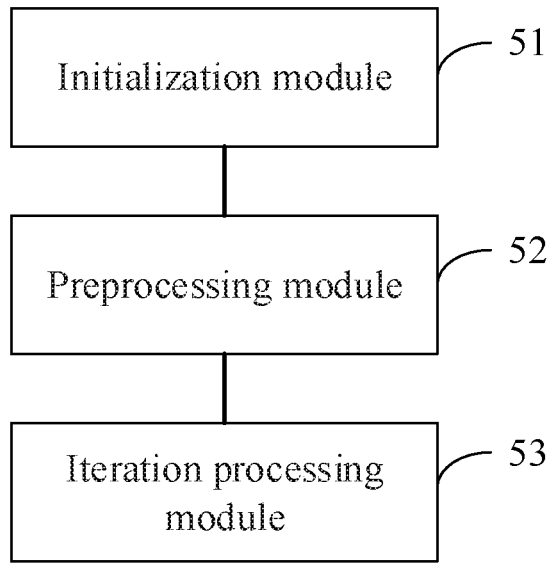
FIG. 5 is a schematic structural diagram of a system for drawing a brain functional atlas according to an embodiment of the present disclosure.

Referring to FIG. 5, an embodiment of the present disclosure provides a system for drawing a brain functional atlas. The system may include:
an initialization module 51, configured to initialize a brain functional atlas of an individual by using a brain functional atlas template to obtain an initial individualized brain functional atlas, the initial individualized brain functional atlas dividing a brain into a plurality of functional areas;
a preprocessing module 52, configured to divide the initial individualized brain functional atlas into a plurality of large areas, each large area including a plurality of functional areas; and
an iteration processing module 53, configured to enter iteration, each iteration process including: calculating a connection degree between each voxel in each large area and each functional area in the large area in sequence, and adjusting each voxel to a functional area having the highest connection degree with the voxel until all voxels are adjusted; and end the iteration when an ending condition is satisfied to obtain a final individualized brain functional atlas.

It can be understood that the functions of each functional module of the system for drawing the brain functional atlas according to the embodiment of the present disclosure may be specifically implemented according to the method in the above method embodiments, and the specific implementation process may refer to the relevant descriptions in the above method embodiment, and will not be repeated herein.

It can be understood that the system for drawing the brain functional atlas according to embodiments of the present disclosure may adopt different implementation forms.

In one aspect, the system may be implemented via a local computer device such as a server. The server obtains functional magnetic resonance scan data from a magnetic resonance device, performs calculation processing, and obtains the final individualized brain functional atlas, and may further generate and output a corresponding report and/or image showing functional partitions of the brain.

In another aspect, the system may also be implemented via a cloud computing platform First, the server obtains the functional magnetic resonance scan data from the magnetic resonance device, and uploads the data to the cloud platform. Then, the cloud platform performs calculation processing to obtain the final individualized brain functional atlas, and may further generate and output the corresponding report and/or image showing the function partitions of the brain. The cloud platform may also send the final individualized brain functional atlas, report and/or image back to the server.

In yet another aspect, the system for drawing the brain functional atlas may also be implemented via a data processing system composed of the server and the cloud computing platform. First, the server may obtain the functional magnetic resonance scan data from the magnetic resonance device, and cooperate with the cloud platform to perform calculation processing to obtain the final individualized brain functional atlas, and may further generate and output the corresponding report and/or image showing the functional partitions of the brain.

Therefore, in some feasible implementations of the present disclosure, the system for drawing the brain functional atlas is provided. According to the system, by performing iterative calculations on the initial individualized brain functional atlas, and continuously adjusting a functional area to which each voxel belongs via the iterative process, a high-precision individualized brain functional atlas can be drawn finally, and high stability, high reliability, and low noise can be achieved under different precisions or resolutions. In the practice of the present disclosure, the whole brain may be divided into 56 functional areas, 112 functional areas, 213 functional areas and other different precisions, and results are stable and reliable, and have been successfully clinically verified.

Figure 6:
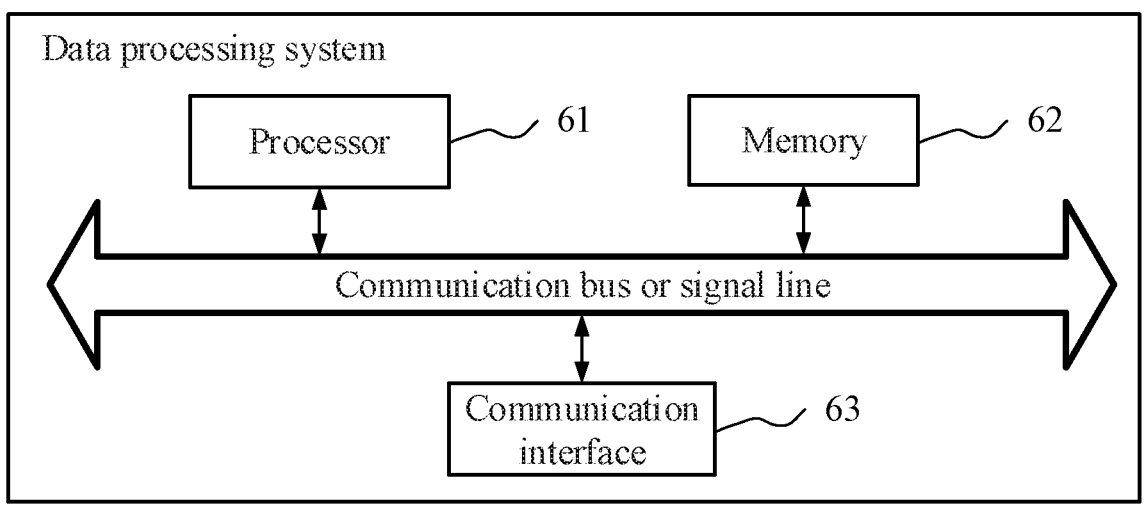
FIG. 6 is a schematic structural diagram of a data processing system according to an embodiment of the present disclosure.

Referring to FIG. 6, an embodiment of the present disclosure further provides a data processing system 60. The system may include:
a processor 61, a memory 62, a communication interface 63, and a bus 64.

The processor 61, the memory 62, the communication interface 63, and the bus 64 are in mutual communication. The communication interface 63 is configured to receive and send data. The memory 62 is configured to store computer-executable instructions. When the data processing system is running, the processor 61 executes the computer-executable instructions stored in the memory 62 to enable the data processing system to implement the method for drawing the brain functional atlas according to the above method embodiments.

The data processing system 60 may be composed of a local computer device such as a local server, or a cloud computing platform, or may be composed of both.

Referring to FIGS. 7-A to 7-C, an embodiment of the present disclosure further provides a medical image processing system. The medical image processing system includes: a data collection system 71, a data output interaction system 72, and the above data processing system. The data processing system includes a local server 73 and/or a cloud computing platform 74.

The data collection system 71 includes a magnetic resonance device, and is configured to collect functional magnetic resonance scan data of an individual, and upload the collected data to the data processing system.

The data processing system is configured to implement the method for drawing the brain functional atlas according to the above embodiment in FIG. 1 to obtain a final individualized brain functional atlas, and generate a corresponding data processing result such as a report and/or image based on the final individualized brain functional atlas.

The data output interaction system 72 includes a display device, an input and output device, etc., and is configured to obtain the data processing result in the form of report and/or image from the data processing system, and display the data processing result.

The data processing system may only include the local server, as shown in FIG. 7-A, or may only include the cloud computing platform, as shown in FIG. 7-B, or may include both the local server and the cloud computing platform, as shown in FIG. 7-C.

When the data processing system includes both the local server and the cloud computing platform, the local server and the cloud computing platform jointly implement the method for drawing the brain functional atlas provided by the present disclosure based on load balancing strategies and/or shared strategies.

The interaction relationship between the local server and the cloud computing platform may include followings.

1. The cloud computing platform does work that may not be completed by the local server. One of the load balancing strategies between the cloud computing platform and the local server may be, for example: when the load of the local server exceeds a certain set value, such as 70%, new work enters the cloud computing platform for processing.
2. When a user has sharing requirements or other location needs, the work may be handed over to the cloud computing platform.

An embodiment of the present disclosure further provides a computer storage medium, and the computer storage medium is a non-transitory computer-readable storage medium storing one or more programs. The one or more programs include computer-executable instructions that, when executed by a data processing system including a processor, enable the data processing system to implement the method for drawing the brain functional atlas according to the above method embodiments.

It should be noted that, for simple description, the above method embodiments are expressed as a series of action combinations, however, those skilled in the art should understand that the present disclosure is not limited by the described action sequences, because some steps may be performed in other order or simultaneously according to the present disclosure. In addition, those skilled in the art also should understand that the embodiments described in the specification all belong to preferred embodiments, and related actions and modules are not certainly necessary to the present disclosure.

Those skilled in the art can clearly understand that, for the convenience and brevity of description, for the specific working process of the system and apparatus described above, please refer to the corresponding process in the above method embodiments. For the parts that are not described in detail in an embodiment, please refer to the related descriptions of other embodiments.

In the embodiments provided by the present application, it should be understood that the disclosed system, apparatus and method may be implemented in other manners. For example, the apparatus embodiment described above is only illustrative. For example, the division of units is only a logical function division, while in actual implementation, there may be other division manners, for example, a plurality of units or modules may be combined or integrated into another system, or some features may be ignored or not implemented. In addition, the shown or discussed mutual coupling or direct coupling or communicative connection may be achieved via some interfaces, and indirect coupling or communicative connection of apparatuses or units may be in electrical, mechanical or other forms.

Units described as separate components may or may not be physically separated, and components shown as units may or ay not be physical units, that is, they may be located in one place, or distributed to a plurality of network units. Some or all of the units may be selected according to actual needs to achieve the purpose of the solutions of the embodiments.

In addition, each functional unit in each embodiment of the present disclosure may be integrated into one processing unit, or each unit may exist physically alone, or two or more units may be integrated into one unit. The above integrated units may be implemented in the form of hardware or software functional units.

If the integrated units are implemented in the form of software functional units and are sold or used as independent products, the units may be stored in a computer readable storage medium. Based on the understandings, the technical solution of the present disclosure is essentially or the part that contributes to the prior art or the whole or part of the technical solution may be embodied in the form of a software product. The computer software product is stored in a storage medium and includes a plurality of instructions to enable a computer device (a personal computer, a server, a network device, etc.) to execute all or part of the steps of the method embodiments. The above storage medium includes: a USB flash disk, a mobile hard disk, a Read-Only Memory (ROM), a Random Access Memory (RAM), a disk, or an optical disk or other media capable of storing program codes.

The method and system for drawing the brain functional atlas provided by the embodiments of the present disclosure have been described in detail above. The principles and implementations of the present disclosure are described herein using specific examples. The descriptions of the above embodiments are only used to help understand the method and the core idea of the present disclosure; and meanwhile, for those ordinary skilled in the art, the specific implementation and application scope may be changed according to the idea of the present disclosure. In conclusion, the content of the specification shall not be construed as limiting the present disclosure.

What is claimed is:

1. A method for drawing an individualized brain functional atlas, comprising:
   initializing a brain functional atlas of an individual by using a brain functional atlas template to obtain an initial individualized brain functional atlas, the initial individualized brain functional atlas dividing a brain into a plurality of functional areas;
   dividing the initial individualized brain functional atlas into a plurality of large areas, each of the large areas comprising a plurality of functional areas;
   entering an iteration, the iteration comprising: calculating a connection degree between each voxel in each of the large areas and each of the functional areas in the each of the large areas in sequence, and adjusting each voxel to a functional area having the highest connection degree with the each voxel until all voxels are adjusted; and
   ending the iteration to obtain a final individualized brain functional atlas in response to an ending condition being satisfied.

2. A method for drawing a group level brain functional atlas, comprising:
   obtaining brain magnetic resonance scanning data of a group of people;
   dividing a brain into a plurality of large areas;
   calculating a group level functional connectivity profile in each of the large areas, the group level functional connectivity profile being a functional connectivity matrix of all voxels in each of the large areas and N interest regions in each of the large areas, and N being a natural number;
   dividing each of the large areas into a plurality of fine-grained functional partitions via a clustering algorithm based on the group level functional connectivity profile as a feature;
   comprehensively evaluating an index of the clustering algorithm and an index of maximization functional homogeneity to determine a quantity of local optimal partitions; and
   merging the fine-grained functional partitions in each of the large areas via a merging algorithm to create the group level brain functional atlas of the whole brain.

3. A data processing system, comprising a processor and a memory, wherein
   the memory is configured to store computer-executable instructions, and when the data processing system is running, the processor executes the computer-executable instructions stored in the memory to enable the data processing system to implement followings for drawing the brain functional atlas;
   initializing a brain functional atlas of an individual by using a brain functional atlas template to obtain an initial individualized brain functional atlas, the initial individualized brain functional atlas dividing a brain into a plurality of functional areas;
   dividing the initial individualized brain functional atlas into a plurality of large areas, each of the large areas comprising a plurality of functional areas;
   entering an iteration, the iteration comprising: calculating a connection degree between each voxel in each of the large areas and each of the functional areas in the each of the large areas in sequence, and adjusting each voxel to a functional area having the highest connection degree with the each voxel until all voxels are adjusted; and
   ending the iteration to obtain a final individualized brain functional atlas in response to an ending condition being satisfied.

4. The method according to claim 1, wherein
   the iteration comprises:
   calculating a reference time series signal of each of the functional areas based on time series signals of all voxels in the each of the functional areas;
   determining an unadjusted voxel as a current voxel;
   calculating a correlation value between a time series signal of the current voxel and a reference time series signal of each of the functional areas in a current large area, the correlation value serving as a connection degree between the current voxel and each of the functional areas in the current large area, and the current large area being a large area to which the current voxel belongs;
   adjusting the current voxel to a functional area having the highest connection degree with the current voxel;
   judging whether all voxels have been adjusted once, and returning to the determining an unadjusted voxel as a current voxel in response to all voxels not being adjusted once; and
   ending the iteration in response to all voxels being adjusted once.

5. The method according to claim 4, wherein
   before the entering iteration, the method further comprises: initializing a credibility of each of the voxels;
   after the adjusting the current voxel to the functional area having the highest connection degree with the current voxel, the method further comprises: updating a credibility of the current voxel; and
   the calculating a reference time series signal of each of the functional areas comprises: calculating an average value of time series signals of all voxels with a credibility not lower than a preset threshold in each of the functional areas as the reference time series signal of the functional area, or calculating a median of time series signals of all voxels with a credibility not lower than a preset threshold in each functional area as the reference time series signal of the functional area.

6. The method according to claim 5, wherein the updating the credibility of the current voxel comprises:
   selecting a largest correlation value and a second largest correlation value from calculated correlation values of the time series signal of the current voxel and the reference time series signal of each of the functional areas in the current large area; and
   calculating and updating the credibility of the current voxel, the credibility of the current voxel being equal to a ratio of the largest correlation value to the second largest correlation value.

7. The method according to claim 1, wherein the ending the iteration comprises:
   ending the iteration in response to a preset iteration frequency or convergence criterion being reached.

8. The method according to claim 1, further comprising: preselecting or generating a group level brain functional atlas as the brain functional atlas template, comprise:
   dividing the brain into a plurality of large areas;
   calculating a group level functional connectivity profile in each of the large areas, the functional connectivity profile being a functional connectivity matrix of voxels in the each of the large areas and N interest regions in the each of the large area, and N being a natural number;

dividing each of the large areas into a plurality of fine-grained functional partitions via a clustering algorithm based on the functional connectivity profile as a feature;

comprehensively evaluating an index of the clustering algorithm and an index of maximization functional homogeneity to determine a quantity of local optimal partitions; and merging the fine-grained functional partitions in each of the large areas via a merging algorithm to create the group level brain functional atlas of the whole brain as the required brain functional atlas template.

9. A non-transitory computer-readable storage medium storing one or more programs, wherein the one or more programs comprise computer-executable instructions that, when executed by a data processing system comprising a processor, enable the data processing system to implement the method for drawing the brain functional atlas according to claim 1.

10. The method according to claim 2, wherein the calculating the group level functional connectivity profile comprises:

calculating individualized functional connectivity profiles in each of the large areas, the group level functional connectivity profile being the functional connectivity matrix of the voxels in the each of the large areas and the N interest regions in the each of the large areas, and N being a natural number; and calculating an average value of all individualized functional connectivity profiles in each of the large areas to obtain the group level functional connectivity profile.

11. A medical image processing system, comprising: a data collection system, a data output interaction system, and the data processing system according to claim 3, wherein the data collection system is configured to collect magnetic resonance scanning data of an individual, and upload collected data to the data processing system, the magnetic resonance scanning data comprising functional magnetic resonance scanning data and/or structural magnetic resonance scanning data;

the data processing system is configured generate a corresponding report and/or image based on the final individualized brain functional atlas;

the data output interaction system is configured to obtain the report and/or image from the data processing system, and display the report and/or image; and the data processing system comprises a local server and/or a cloud computing platform, and in response to the data processing system comprising both the local server and the cloud computing platform, the local server and the cloud computing platform jointly implement the method for drawing the brain functional atlas according to claim 1 based on load balancing strategies and/or shared strategies.

12. The data processing system according to claim 3, wherein the iteration comprises:

calculating a reference time series signal of each of the functional areas based on time series signals of all voxels in the each of the functional areas;

determining an unadjusted voxel as a current voxel;

calculating a correlation value between a time series signal of the current voxel and a reference time series signal of each of the functional areas in a current large area, the correlation value serving as a connection degree between the current voxel and each of the functional areas in the current large area, and the current large area being a large area to which the current voxel belongs;

adjusting the current voxel to a functional area having the highest connection degree with the current voxel;

judging whether all voxels have been adjusted once, and returning to the determining an unadjusted voxel as a current voxel in response to all voxels not being adjusted once; and ending the iteration in response to all voxels being adjusted once.

13. The data processing system according to claim 12, wherein the processor executes the computer-executable instructions stored in the memory to enable the data processing system to implement followings:

before the entering iteration, initializing a credibility of each of the voxels;

after the adjusting the current voxel to the functional area having the highest connection degree with the current voxel, the method further comprises: updating a credibility of the current voxel; and the calculating a reference time series signal of each of the functional areas comprises: calculating an average value of time series signals of all voxels with a credibility not lower than a preset threshold in each of the functional areas as the reference time series signal of the functional area, or calculating a median of time series signals of all voxels with a credibility not lower than a preset threshold in each functional area as the reference time series signal of the functional area.

14. The data processing system according to claim 13, wherein the updating the credibility of the current voxel comprises:

selecting a largest correlation value and a second largest correlation value from calculated correlation values of the time series signal of the current voxel and the reference time series signal of each of the functional areas in the current large area; and calculating and updating the credibility of the current voxel, the credibility of the current voxel being equal to a ratio of the largest correlation value to the second largest correlation value.

15. The data processing system according to claim 3, wherein the ending the iteration comprises:

ending the iteration in response to a preset iteration frequency or convergence criterion being reached.

16. The data processing system according to claim 3, wherein the processor executes the computer-executable instructions stored in the memory to enable the data processing system to implement followings: preselecting or generating a group level brain functional atlas as the brain functional atlas template, comprise:

dividing the brain into a plurality of large areas;

calculating a group level functional connectivity profile in each of the large areas, the functional connectivity profile being a functional connectivity matrix of voxels in the each of the large areas and N interest regions in the each of the large area, and N being a natural number;

dividing each of the large areas into a plurality of fine-grained functional partitions via a clustering algorithm based on the functional connectivity profile as a feature;

comprehensively evaluating an index of the clustering algorithm and an index of maximization functional homogeneity to determine a quantity of local optimal partitions; and merging the fine-grained functional partitions in each of the large areas via a merging algorithm to create the group level brain functional atlas of the whole brain as the required brain functional atlas template.

\* \* \* \* \*